(12) United States Patent
Hafez et al.

(10) Patent No.: US 11,135,018 B2
(45) Date of Patent: Oct. 5, 2021

(54) METHOD FOR TREATING AND REPAIRING KNEE FRACTURES RESULTING FROM BENIGN TUMORS USING PATIENT-SPECIFIC ELECTRONIC TEMPLATES

(71) Applicant: Mahmoud Alm El Din Hafez, Giza (EG)

(72) Inventors: Mahmoud Alm El Din Hafez, Giza (EG); Ahmed Abdel Moghny Salem, Giza (EG)

(73) Assignee: Mahmoud Alm El Din Hafez, Giza (EG)

( * ) Notice: Subject to any disclaimer, the term of this patent is extended or adjusted under 35 U.S.C. 154(b) by 0 days.

(21) Appl. No.: 16/758,208

(22) PCT Filed: Oct. 22, 2018

(86) PCT No.: PCT/EG2018/000022
§ 371 (c)(1),
(2) Date: Apr. 22, 2020

(87) PCT Pub. No.: WO2019/076421
PCT Pub. Date: Apr. 25, 2019

(65) Prior Publication Data
US 2020/0337775 A1  Oct. 29, 2020

(30) Foreign Application Priority Data

Oct. 22, 2017 (EG) .................................. 2017100028
Apr. 19, 2018 (EG) .................................. 2018040655

(51) Int. Cl.
| *A61B 17/58* | (2006.01) |
| *A61B 17/60* | (2006.01) |
| *A61F 2/00*  | (2006.01) |
| *A61B 34/10* | (2016.01) |
| *A61B 17/17* | (2006.01) |
| *A61B 90/00* | (2016.01) |
| *A61B 17/56* | (2006.01) |

(52) U.S. Cl.
CPC .......... *A61B 34/10* (2016.02); *A61B 17/1728* (2013.01); *A61B 17/1764* (2013.01); *A61B 2017/564* (2013.01); *A61B 2017/568* (2013.01); *A61B 2034/108* (2016.02); *A61B 2090/3762* (2016.02)

(58) Field of Classification Search
CPC combination set(s) only.
See application file for complete search history.

(56) References Cited

FOREIGN PATENT DOCUMENTS

| EP | 2529677 A1 | 12/2012 |
| ES | 2554568 A2 | 12/2015 |
| WO | 2012049692 A1 | 4/2012 |

*Primary Examiner* — Sameh R Boles
(74) *Attorney, Agent, or Firm* — Dickinson Wright PLLC; Andrew D. Dorisio

(57) ABSTRACT

This invention relates to a method for osteotomy correction and fixation of tumor fracture by placing a patient specific template over the osteotomy or the tumor locations, which produced by a certain preoperative planning and depends on a highlighted land marks on the bone surface. The patient specific template includes a holes and slots for fixation and resection of the bone. The patient specific template guide the surgeon to the boundaries of tumor along the bone. The planning and the design of the patient specific template depend on the tibial mechanical axis.

10 Claims, 6 Drawing Sheets

METHOD FOR TREATING AND REPAIRING KNEE FRACTURES RESULTING FROM BENIGN TUMORS USING PATIENT-SPECIFIC ELECTRONIC TEMPLATES

This application claims the benefit of Egyptian Provisional application No. 28/2017 filed on Oct. 22, 2017 and Egyptian Patent Application No. 655/2018 on Apr. 19, 2018

TECHNICAL FIELD

The present invention relates to a patient-specific electronic template for treating and repairing knee fractures resulting from benign tumors. The said template is designed to fit the medical case as revealed by tomography scan (CT scan), mechanical axis of the bone, tumor position and markers on the affected bone's surface for fixing the template later on the bone. 3D printers are used for template manufacturing.

DISADVANTAGES OF CURRENT TECHNOLOGIES

Traditional medical tools are used for corrective surgeries of fractures related to bone deformities and benign tumors. Therefore, their application is limited to highly skilled and experienced surgeons.

Surgeons face a number of medical and surgical challenges before and during surgery. Such challenges are raised mainly due to the use of two-dimensional X-rays, as well as other types of imaging, such as CT scanning and MRI. In fact, the available scan types alone are not enough for avoiding the possible medical and surgical difficulties during such corrective surgeries.

Challenges which surgeons face may be inability to accurately determine the tumor extension in the bone using the two-dimensional ray scan that does not show the accurate location of the tumor as well as its internal extension. Hence, the surgeon would be unable to locate the correct place for metal disc fixation for correcting tumor-related bone deformation.

The second challenge is to avoid inserting a fixation screw of the metal disc into tumor area by mistake. Defining the tumor border and size requires high experience and efficient tools. The surgeon's inability to determine the size and shape of the metal disc in advance makes it difficult to find the disc that most fits the bone's anatomical morphology and tumor dimensions. As a result, the used metal disc would be unfit to the patient's bone, leading to post-surgery complications that may affect the patient's ability to perform daily activities.

The current adopted technology is problematic in case of bone tumors in pediatrics or young age. The pediatric bone growth, leading to the change of the metal disc location, makes the bone prone to sudden fractures.

In brief, this type of surgery must be performed by long-experienced surgeons. Avoiding the raised surgical challenges, especially for junior inexperienced surgeons, requires a long time of practice, training, and acquiring skills.

Accordingly, there is a dire need to a new method and approach for solving the current technical problems. The inventive electronic template provides a solution for the current problems. It is used for specifying the position, alignment, and size of the metal disc and its related fixation screws in addition to accurately determining the position and dimensions of the tumor and its extension in the bone. In this way, the common surgical difficulties are avoided.

DETAILED DESCRIPTION OF THE INVENTION

The present invention relates to a patient-specific electronic template for treating and repairing knee fractures resulting from benign tumors. The inventive template specifies the tumor extensions and depth, and the positions of the metal disc's fixation as well as its size and shape. The said electronic template is designed to fit the medical case as revealed by CT scan, mechanical axis of the bone, tumor position and markers on the affected bone's surface for fixing the template later to the bone.

Since the template is designed according to the patient's CT scan, it cannot be used for other patients. It is a unique template carrying the patient's data, such as his name, the disc size, whether it is the right or the left knee. It also has an anatomical structure identical to that of the patient's bone, as described later in details.

The template has a number of openings whose locations and diameters are accurately chosen for fixation of the template to the bone surface and for making paths for metal disc fixation later. The template includes two indicators for specifying the tumor location and dimensions to help the surgeon to locate the tumor and determine its dimensions and depth on the bone.

Being designed according to a computer-assisted surgical planning, the template allows the surgeon to make accurate paths for fixation of the metal disc to the bone. First, an X-ray image or a CT scan is inputted into the program to be transformed to a three-dimensional model for the bone including all anatomical markers on the bone surface as well as the tumor location, dimensions and depth. After converting the two-dimensional ray into a three-dimensional model for the bone, a surgical pre-planning is done by a special program. The tumor location and dimensions are determined, as well as the location, alignment, size, shape and inclination angle of the metal disc to be fixed to the bone for correcting its position.

The template is designed according to the dimensions, size and shape of the metal disc. Additional openings are made in the template for being fixed to the proper location on the bone during surgery. The fixation openings of the template have different locations and inclination angles relative to the bone and different diameters. Some of the openings have diverged inclination angles while others are perpendicular on the bone; such variation prevents the template displacement. It becomes fixed in its pre-determined position allowing the surgeon to properly locate the metal disc's fixation openings later. The fixation screws' openings help the surgeon to open paths for fixation of the metal disc to the bone while avoiding template displacement.

The topology of the template's internal surface, that matches the bone's outer surface topology, should then be examined. The said topology is identical to that of the bone surface at the templates pre-determined location. Since the bone's topology as well as the anatomical morphology differs from one patient to another, the template fits one patient only. It has a unique internal surface that totally depends on the bone's surface and anatomy, as well as some anatomical markers such as bone protrusion, curvature, or some natural paths on the bone's surface, according to the tumor place. Examples of the natural paths are the tibial tuberosity of the leg bone, two head groove of the shoulder bone, or epicondyle of the thigh bone. Therefore, the template is characterized with an internal surface's topology that prevents its placement in the wrong place. The internal surface's topology only matches the location of the bone—previously determined by the computer program—on which the metal disc should be fixed.

Pre-planning surgeries for treating and repairing knee fractures resulting from benign tumors depends on mechanical and anatomical axes for the bone, the degree of its curvature or deformity resulting from the place, dimensions and depth of the tumor. Depending on these factors as well as the bone dimensions inputted into the program through CT scan pictures, the surgeon specifies the correct size, location, alignment and inclination angle of the metal disc on the bone, as well as the location, level, and inclination angle of screws' fixation openings of the metal disc. The surgeon thus gets a thorough vision of the surgery requirements, the sizes and shapes of the used metal discs, the tumor location, dimensions and depth.

As a result, the surgeon avoids difficulties associated with traditional surgical practices resulting in medical harms, such as mistakenly introducing the metal disc fixation screw into the tumor area due to lack of experience or inability of traditional devices to accurately determine the tumor's borders and area. The surgeon also avoids the difficulty of predetermination of the size and shape of the metal disc that would make the metal disc unfit for the patient's bone, resulting in post-surgery medical complications that would influence the patient's daily activities.

As previously mentioned, the conventional methods are problematic for bone tumors in pediatrics. The pediatric bone growth leads to the change of the metal discs' location, making the bone prone to sudden breakage. Accordingly, corrective surgeries for pediatric bone deformities and fracture resulted from benign tumors are not fully successful.

At this stage, the program searches for the appropriate electronic shape for the template according to the position, alignment and size specified by the surgeon. The topology of the internal template surface matches that of the external bone surface at the targeted fixation location. The electronic template file is sent to a 3D printer to be manufactured and used in real surgeries. The surgeon can choose from different techniques putting into consideration the required quality and the final price.

Unlike conventional tools, the inventive electronic templates are easy to sterilize, easy to carry and handle for its light weight. According to the invention, only one template is used per surgery, while more than 120 components are used in conventional surgical practices.

Figure 1:
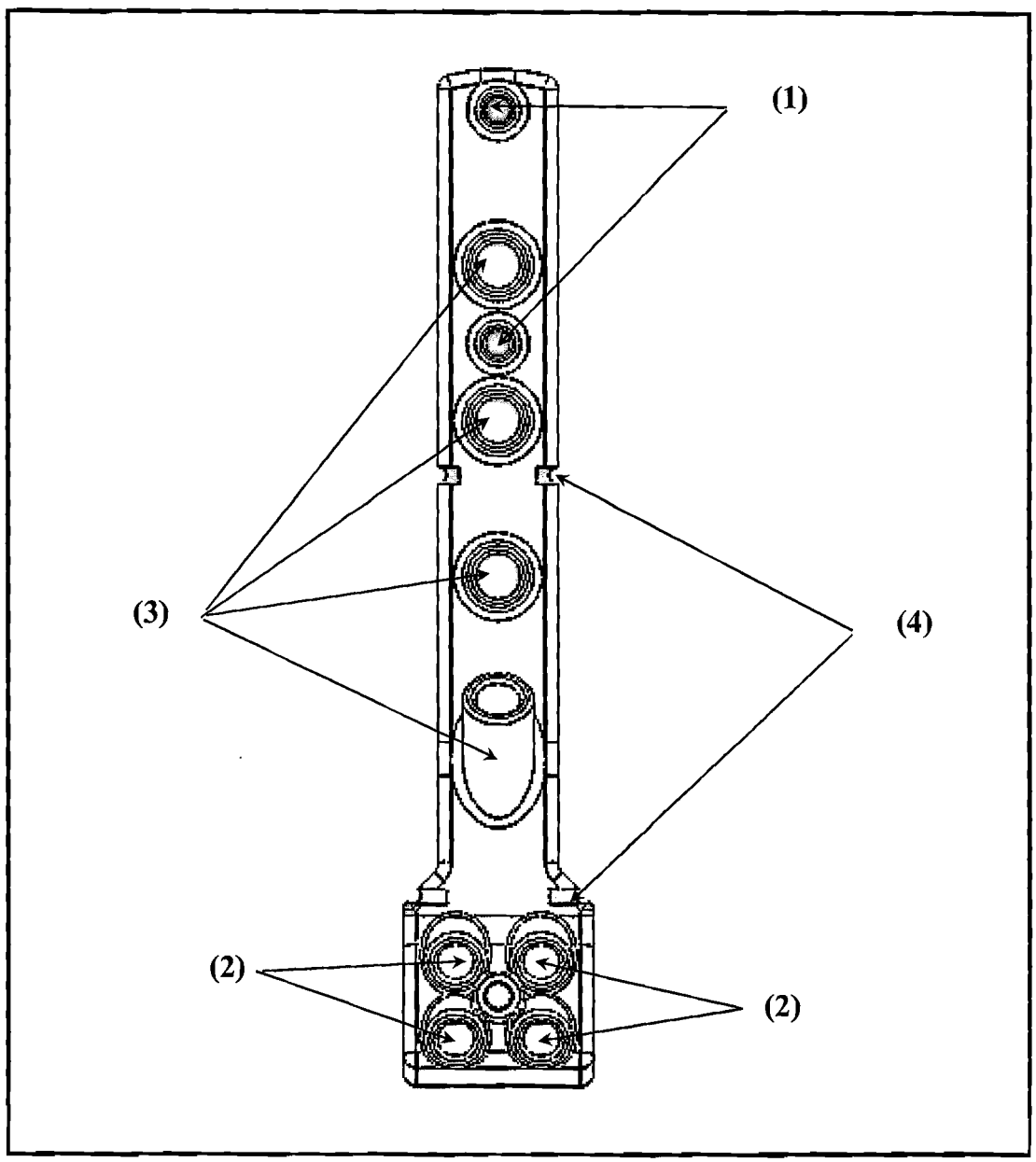
FIG. 1 represents a two-dimensional front view for the inventive template with both perpendicular (1) and inclined (2) fixation screws' openings, as well as holes for making paths for the metal disc fixation screws' openings (3), and indicators for the tumor location (4).
Figure 2:
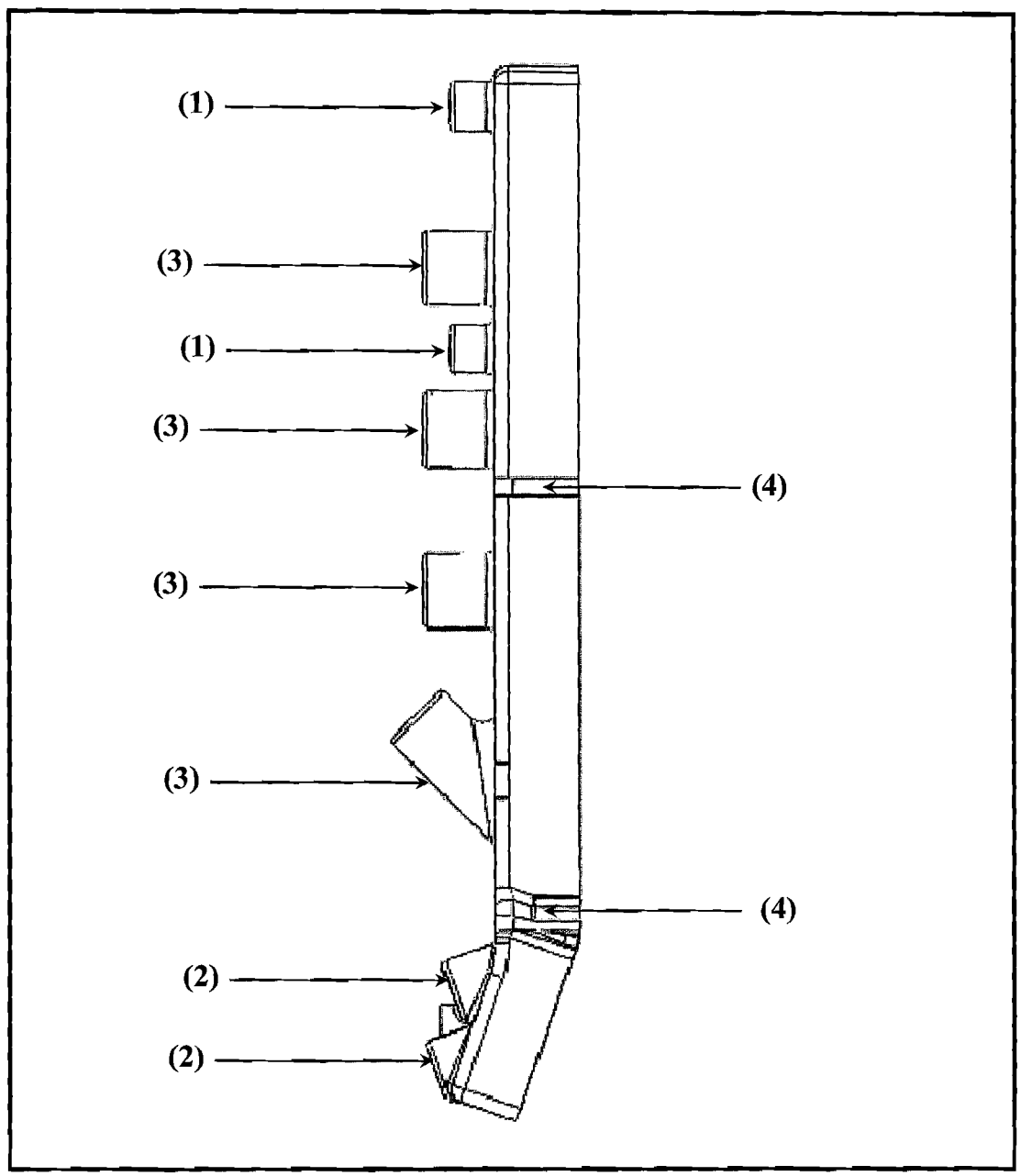
FIG. 2 represents a two-dimensional side elevation for the inventive template with perpendicular fixation screws' openings (1) and inclined (2) fixation screws' openings, as well as holes for making paths for the metal disc fixation openings (3), and indicators for the tumor location (4).
Figure 3:
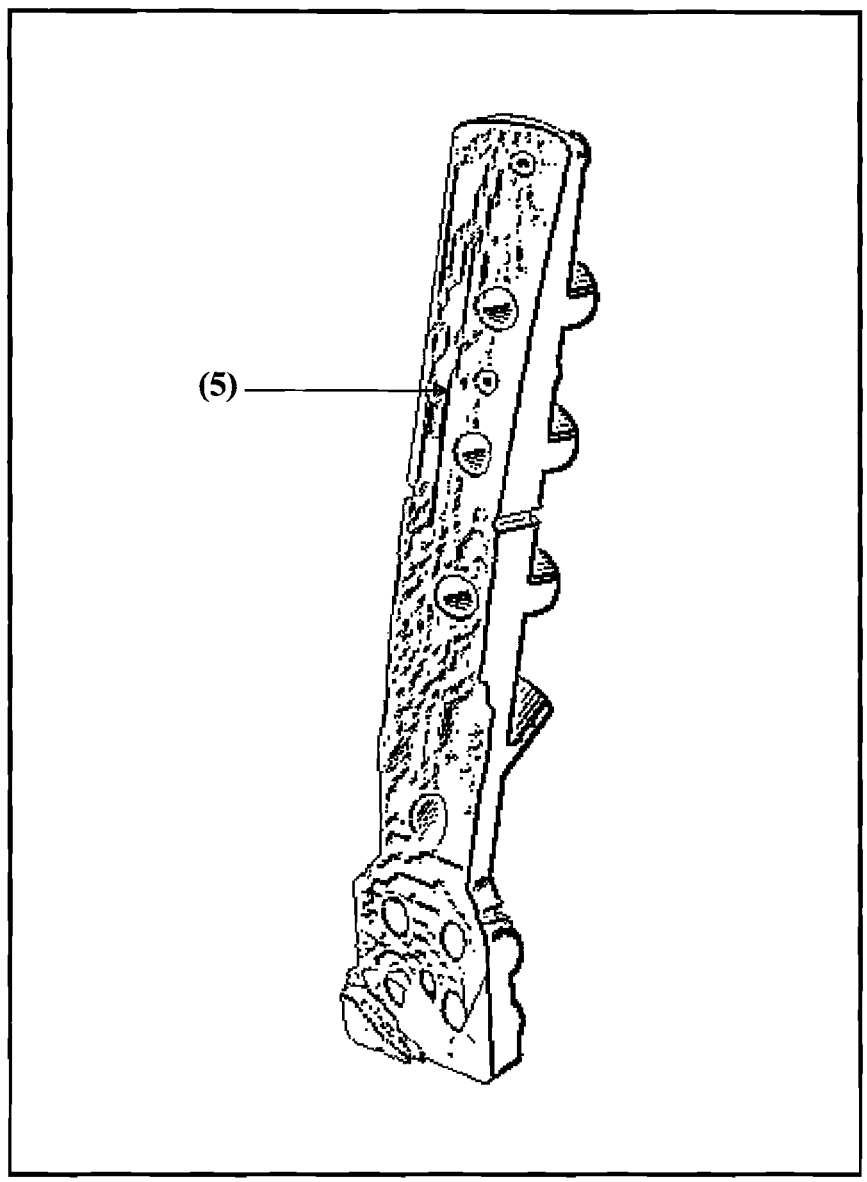
FIG. 3 represents a three-dimensional perspective for the template; the internal surface of the templates appears with a topology matching that of the external bone surface (5).
Figure 4:
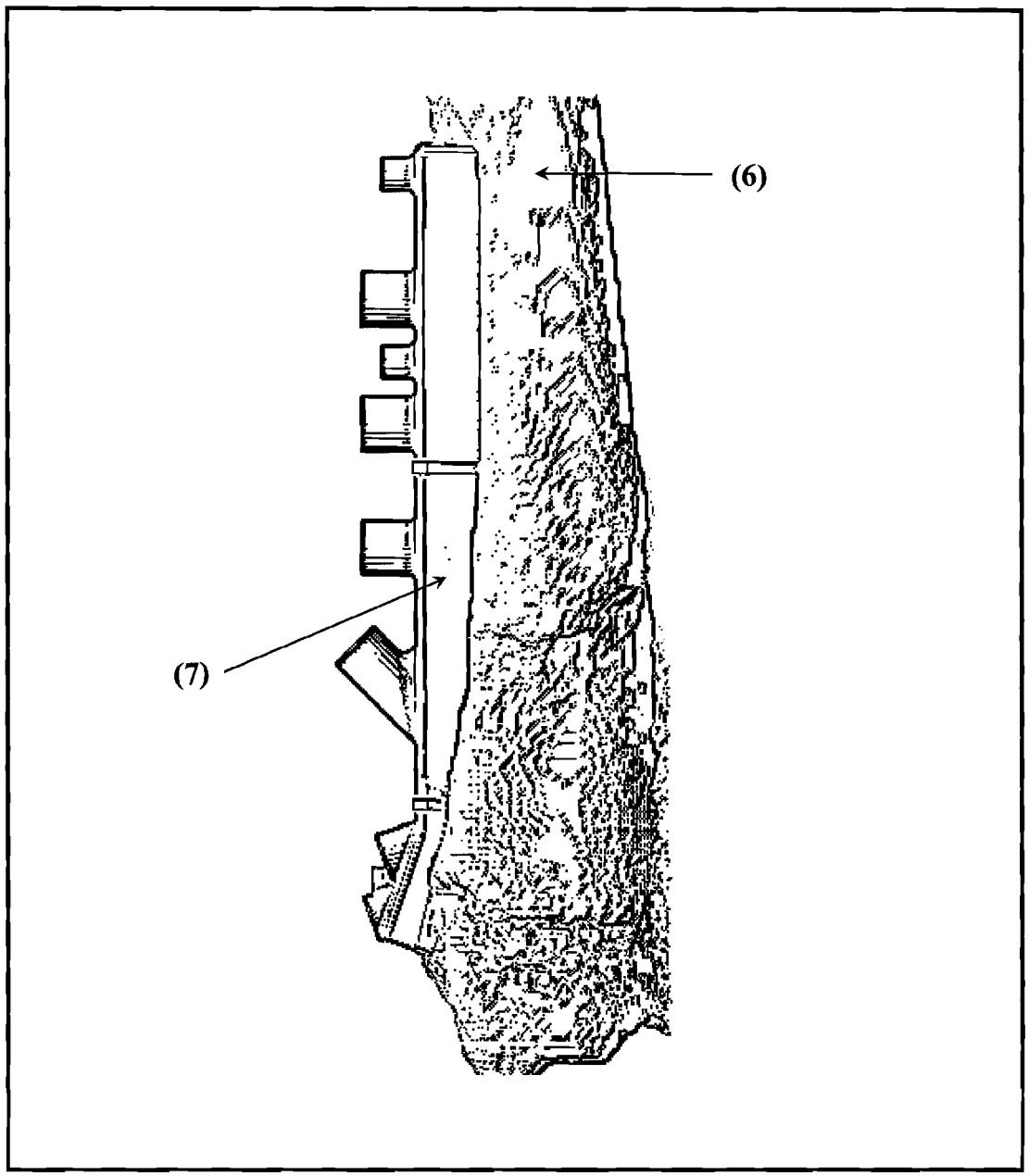
FIG. 4 represents a two-dimensional side elevation for the template (7) fixed to the bone (6).
Figure 5:
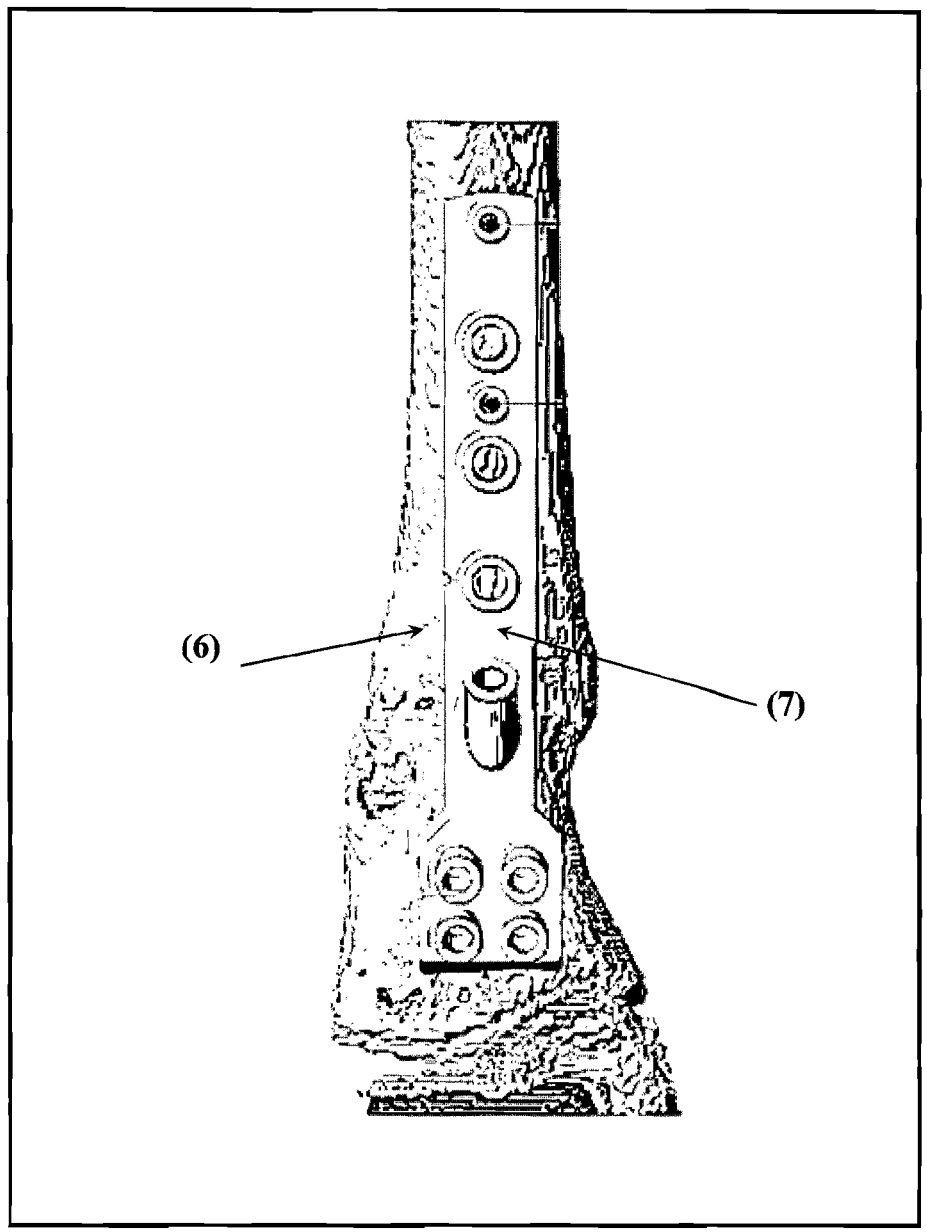
FIG. 5 represents a two-dimensional side elevation for the template (7) fixed to the bone (6).
Figure 6:
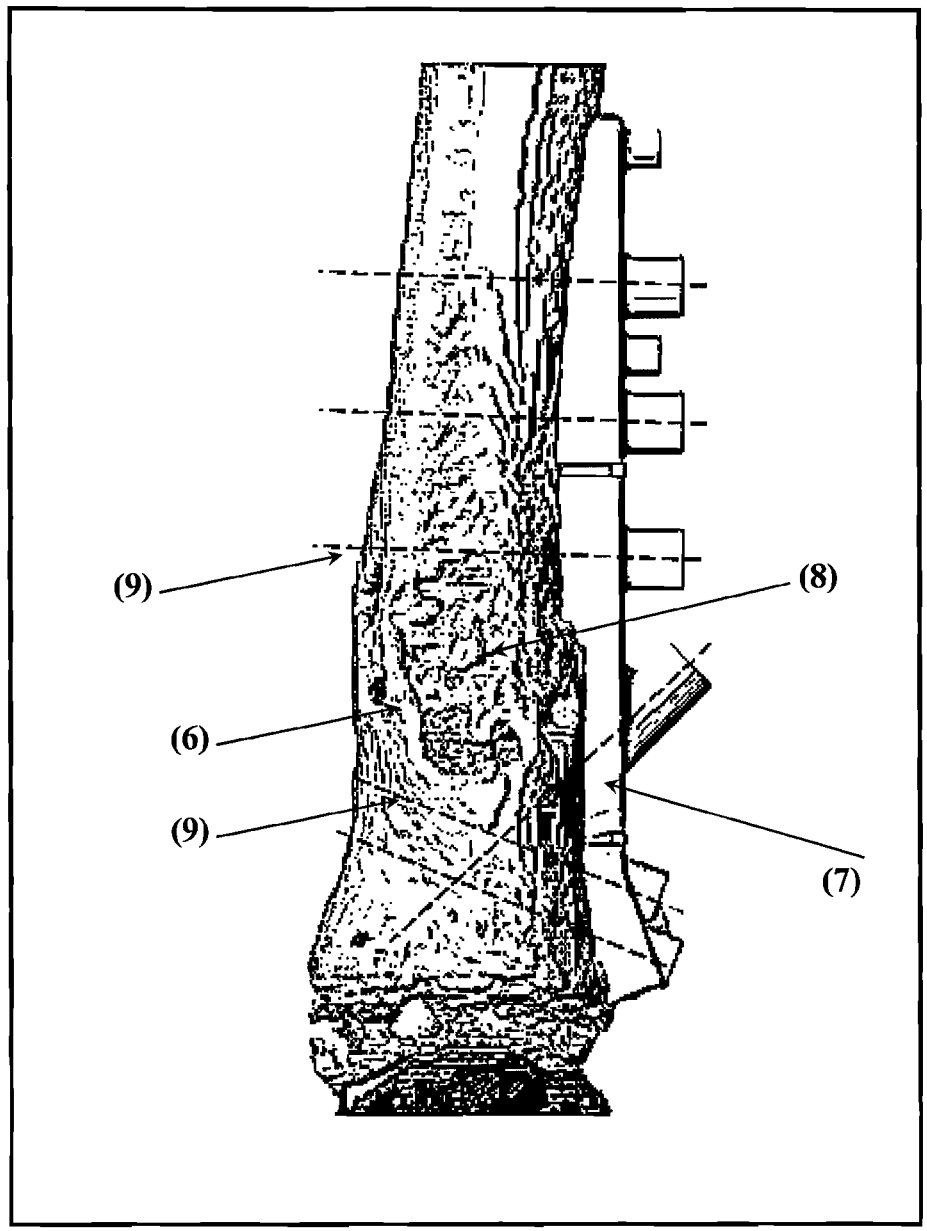
FIG. 6 represents a two-dimensional side elevation for the template (7) fixed to the bone (6) with tumor location (8) and tumor location indicators (9)

The invention claimed is:

1. A method and a patient-specific electronic template for treating and repairing knee fractures resulting from benign tumors. The electronic templates are designed according to the patient's case as determined by CT scan, mechanical axis of the bone and markers on the affected bones' surface. The said markers are also used for template fixation to the bone later. The template contains openings and conduits for fixation and for making the necessary surgical cuts for repairing and fixing the fracture. It also includes indicators for locating the tumor as well as fixation screws' openings for metal supports used in surgery.

2. A template according to claim (1), whereas the template comprise of cutting openings of specific dimensions identical to the openings of the metal disc to be fixed to the bone.

3. A template according to claim (1), characterized with fixation screws' openings for template fixation to the bone.

4. A template according to claim (1), characterized with an internal surface that matches the bone's surface on which it would be fixed.

5. A template according to claim (1), whereas the template's internal surface is made identical to the bone's external surface by the aid of the anatomical morphology of the bone as well as the anatomical markers on its surface. The used anatomical markers are the bone's conical shape, the bone protrusion or curvature or some natural paths on the bone's surface, depending on the tumor place, such as the tuberosity of tibia of the leg bone, the two head grooves of the shoulder bone, or epicondyle of the thigh bone.

6. A template according to claim (1), whereas it comprises of upper fixation screws' openings perpendicular on the leg bone's surface, and lower fixation screws' openings inclined with an angle relative to the bone surface. These openings prevent the template displacement; the template would be fixed in its proper position, as pre-determined by the computer program. In this way, accurate surgeries of treating and repairing knee fractures resulting from benign tumors would be performed.

7. A template according to claim (1), whereas it contains perpendicular and inclined fixation openings relative to the bone. The template's openings match those of the metal disc that would be fixed, enabling the surgeon to make paths for fixation screws in the metal disc.

8. A template according to claim (1) whereas it contains indicators to guide the surgeon to the tumor borders and dimensions. Thus, the penetration of the metal disc's screws into the tumor area would be avoided.

9. A template according to claim (1), whereas the surgical pre-planning depends on the CT scan of the patient undergoing surgery for treating and repairing knee fractures resulting from benign tumors. CT scan picture is transformed into a three-dimensional model for the bone, including all details related to the shape, anatomy and anatomical markers of the bone.

10. A template according to claim (1), whereas it is made from a nylon which is light in weight and can be sterilized. It is a medical material approved by American Food and Drug Administration (FDA).

* * * * *